(12) United States Patent
Dobrynin et al.

(10) Patent No.: US 10,500,407 B2
(45) Date of Patent: Dec. 10, 2019

(54) APPARATUS FOR ATMOSPHERIC PRESSURE PIN-TO-HOLE SPARK DISCHARGE AND USES THEREOF

(71) Applicants: Danil V. Dobrynin, Philadelphia, PA (US); Alexander Fridman, Philadelphia, PA (US); Young I. Cho, Cherry Hill, NJ (US); Gregory Fridman, Philadelphia, PA (US); Gennady Friedman, Philadelphia, PA (US)

(72) Inventors: Danil V. Dobrynin, Philadelphia, PA (US); Alexander Fridman, Philadelphia, PA (US); Young I. Cho, Cherry Hill, NJ (US); Gregory Fridman, Philadelphia, PA (US); Gennady Friedman, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 160 days.

(21) Appl. No.: 15/333,862

(22) Filed: Oct. 25, 2016

(65) Prior Publication Data

US 2017/0296836 A1    Oct. 19, 2017

Related U.S. Application Data

(62) Division of application No. 13/256,556, filed as application No. PCT/US2010/027408 on Mar. 16, 2010, now Pat. No. 9,511,240.

(Continued)

(51) Int. Cl.
*A61N 1/44* (2006.01)
*A61N 1/04* (2006.01)

(52) U.S. Cl.
CPC .............. *A61N 1/44* (2013.01); *A61N 1/0468* (2013.01); *A61N 1/0472* (2013.01)

(58) Field of Classification Search
CPC ...... A61N 1/44; A61N 1/0468; A61N 1/0472; B01D 46/00; B01D 46/0084; B01D 53/02;

(Continued)

(56) References Cited

U.S. PATENT DOCUMENTS

| 4,766,318 A | 8/1988 | Adler-Golden et al. |
| 4,895,169 A | 1/1990 | Heath |

(Continued)

FOREIGN PATENT DOCUMENTS

| EP | 1803464 A1 | 7/2007 |
| RU | 2285358 C2 | 10/2006 |

OTHER PUBLICATIONS

Fridman et al., "Applied Plasma Medicine", Plasma Processes and Polymers, Review, Apr. 2008, 5(6), 503-533.

(Continued)

*Primary Examiner* — Xiuyu Tai
(74) *Attorney, Agent, or Firm* — BakerHostetler

(57) ABSTRACT

Disclosed herein are atmospheric pressure pin-to-hole pulsed spark discharge devices and methods for creating plasma. The devices include a conduit for fluidically communicating a gas, a plasma, or both, therethrough, portion of the conduit capable of being connected to a gas supply, and a second portion of the conduit capable of emitting a plasma; a positive electrode comprising a sharp tip; and a ground plate electrode. Disclosed are methods for treating a skin ulcer using non-thermal plasma include flowing a gas through a cold spark discharge zone simultaneously with the creation of a pulsed spark discharge to give rise to a non-thermal plasma emitted from a conduit, the non-thermal (Continued)

plasma comprising NO; and contacting a skin ulcer with said non-thermal plasma for sufficient time and intensity to give rise to treatment of the skin ulcer.

14 Claims, 7 Drawing Sheets

Related U.S. Application Data

(60) Provisional application No. 61/160,556, filed on Mar. 16, 2009, provisional application No. 61/160,633, filed on Mar. 16, 2009.

(58) Field of Classification Search
CPC ........ B01J 19/088; B01J 20/103; B01J 20/08; B01J 20/041; B01J 20/22; B01J 20/28047; B01J 20/20; B01J 2219/0875; B01J 2219/0883; B01J 2219/0894; B01J 2219/0809; B01J 2219/0801; C01B 21/32; C01B 21/203; A61K 33/00; A61M 15/02; A61M 2202/0275
See application file for complete search history.

(56) References Cited

U.S. PATENT DOCUMENTS

| | | | |
|---|---|---|---|
| 5,396,882 A | | 3/1995 | Zapol |
| 5,603,893 A | | 2/1997 | Gundersen et al. |
| 6,103,190 A | | 8/2000 | Tanimura et al. |
| 6,629,974 B2 * | 10/2003 | Penny | ................. A61B 18/042 128/898 |
| 6,955,790 B2 * | 10/2005 | Castor | ....................... B01J 8/02 422/186.04 |
| 7,250,195 B1 | | 7/2007 | Storey et al. |
| 7,498,000 B2 * | 3/2009 | Pekshev | ................ A61M 15/02 204/179 |
| 2004/0088036 A1 | | 5/2004 | Gilbert |
| 2005/0174062 A1 | | 8/2005 | Tanaka et al. |
| 2006/0058782 A1 | | 3/2006 | Truckai et al. |
| 2006/0155354 A1 | | 7/2006 | Heath |
| 2007/0179497 A1 | | 8/2007 | Eggers et al. |
| 2007/0213700 A1 | | 9/2007 | Davison et al. |
| 2007/0225614 A1 | | 9/2007 | Naghavi et al. |
| 2008/0033506 A1 | | 2/2008 | Flick |
| 2009/0038933 A1 | | 2/2009 | Boutot et al. |

OTHER PUBLICATIONS

PCT Application No. PCT/US2010/027408 : International Preliminary Report on Patentability, dated Sep. 20, 2011, 6 pages.

PCT Application No. PCT/US2010/027408 : International Search Report and Written Opinion of the International Searching Authority, dated May 17, 2010, 8 pages.

* cited by examiner

APPARATUS FOR ATMOSPHERIC PRESSURE PIN-TO-HOLE SPARK DISCHARGE AND USES THEREOF

CROSS-REFERENCE TO RELATED APPLICATIONS

This application is a divisional application of U.S. Non-Provisional patent application Ser. No. 13/256,556, filed Feb. 2, 2012, which is the National Stage of International Application No. PCT/US2010/027408, filed Mar. 16, 2010, which claims the benefit of U.S. Provisional Patent Application No. 61/160,633, filed Mar. 16, 2009, and U.S. Provisional Patent Application No. 61/160,556, also filed Mar. 16, 2009, the contents of which are hereby incorporated in their entirety by reference.

STATEMENT OF FEDERALLY SPONSORED RESEARCH

This invention was made with government support under Contract No. DE-FC26-06NT42724 awarded by the Department of Energy and Contract No. W81XWH-06-1-0742 awarded by the U.S. Army Medical Research Acquisition Activity. The government has certain rights in the invention.

TECHNICAL FIELD

The present invention relates generally to the apparatus and methods of non-thermal plasma generation and uses in treatment of disorders.

BACKGROUND

Effective use of plasma in surgery has been first demonstrated in 1960s: plasma afterglow jet of an inert gas has been applied for tissue sectioning with instant blood coagulation. Because of this, plasma-surgical devices got a long-standing name of "plasma scalpel" in the hospitals.

Significant advancement in the plasma surgery, wound healing and tissue regeneration is due to development of the "Plazon" system based on the jet of hot air plasma rapidly quenched and providing relatively high NO concentration over a long distance with significant therapeutic effect. The "Plazon" generators, which require a large power supply, are the DC arcs with different configurations of the exit channels corresponding to the different applications (blood coagulation, tissue destruction, therapeutic manipulation/stimulation). Due to the DC arcs, the energy consumption rate in the Plazon is high and the temperature of the electrodes becomes excessively high, requiring an active cooling of the electrodes. Main and common elements of the system construction are the liquid-cooled cathode, intra-electrode insert, and anode. Atmospheric air enters the manipulator through the built-in micro-compressor, passes through the plasma arc, heats up and thus accelerates, and exits through the hole in the anode of the plasma-generating module.

A device for generation of plasma stream is reported in RU 2285358 C2. This device for generation of plasma flow contains a nozzle for gas flow around a rod electrode located at the center with a sharpened tip. The plasma stream temperature exponentially decreased with the distance. The temperature is reported to be 60° C. at the output aperture, which temperature is often too hot for uses in biomedical applications. Accordingly, there is a need to create cooler plasma sources that are, e.g., suitable for use in biomedical applications.

SUMMARY

The present invention provides an atmospheric pressure pin-to-hole spark discharge (PHSD) devices and methods suitable for preparing non-thermal (cold) plasmas that can be used for biomedical applications.

Certain aspects of the present invention provides atmospheric pressure pin-to-hole pulsed spark discharge devices, comprising: a conduit for fluidically communicating a gas, a plasma, or both, therethrough, portion of the conduit capable of being connected to a gas supply, and a second portion of the conduit capable of emitting a plasma; a positive electrode comprising a sharp tip, the positive electrode capable of receiving a high voltage from a positive terminal of a capacitative circuit; a ground plate electrode comprising an opening passing through the plate, the opening characterized as having a dimension, d, the ground plate electrode capable of being in electrical communication with ground and a negative electrode of said capacitative circuit, the sharp tip of the positive electrode located proximate to the opening of the ground plate electrode by distance h, the distance h defining a spark zone between the sharp tip of the positive electrode and the opening of the ground plate electrode; wherein the sharp tip of the positive electrode, the opening of the ground plate electrode and the spark zone are located within the second portion of the conduit capable of emitting a plasma; the capacitative circuit comprising positive and negative leads in electrical communication with the positive and negative electrodes, respectively, the positive lead of the capacitative circuit being disposed at a location between the sharp tip of the positive electrode and the positive terminal of the high voltage power supply, and the negative lead of the capacitative circuit being disposed at a location between the opening of the ground plate electrode and the negative terminal of the high voltage power supply, wherein actuation of the high voltage power supply is capable of charging the capacitative circuit to provide a voltage of at least 500 V across the electrodes, the capacitative circuit being capable of creating a pulsed spark discharge at a rate of at least 1 Hz in the spark zone, and wherein flowing a gas through the spark zone simultaneously with the creation of the pulsed spark discharge is capable of giving rise to a non-thermal plasma emitted from the second portion of the conduit.

The present invention also provides methods of creating a non-thermal plasma, comprising: flowing gas through a conduit capable of fluidically communicating a gas, a plasma, or both, therethrough, a portion of the conduit capable of being connected to a gas supply, and a second portion of the conduit capable of emitting a plasma, the conduit comprising therewithin: a positive electrode comprising a sharp tip, the positive electrode capable of receiving a high voltage from a positive terminal of a high voltage power supply; a ground plate electrode comprising an opening passing through the plate, the opening characterized as having a dimension, d, the ground plate electrode capable of being in electrical communication with ground and a negative electrode of said high voltage power supply, the sharp tip of the positive electrode located proximate to the opening of the ground plate electrode by distance h, the distance h defining a spark zone between the sharp tip of the positive electrode and the opening of the ground plate electrode; wherein the sharp tip of the positive electrode, the opening of the ground plate electrode and the spark zone are located within the second portion of the conduit capable of emitting a plasma; and repeatedly charging and discharging a capacitative circuit electrically coupled to a high voltage power supply to provide a voltage of at least 500 V across the positive and ground negative to give rise to a pulsed spark discharge at a rate of at least 1 Hz in the spark zone; and flowing a gas through the spark zone simultaneously with the creation of the pulsed spark discharge to give rise to a non-thermal plasma emitted from the second portion of the conduit.

The present invention does not necessarily require the human body to be used as a second electrode, as is required in certain prior art devices. In the present invention, both the HV electrode and ground electrode can be integrated into one unit.

The present invention may also use a co-axial configuration, where the HV electrode is located at the center of a cylindrical geometry, whereas the outer cylindrical case is used as a grounded electrode.

Alternatively, the present invention can uses two wire electrodes: one being used as the HV electrode and the other being used as the ground electrode.

Certain aspects of the present invention can be used to produce a pulse spark for biomedical applications.

Certain aspects of the present invention can also be used to provide a self-standing plasma discharge device without the use of patient body as a second electrode.

An object of the present invention is to restore blood flow using plasma treatment at tissue affected by ischemic skin ulcer.

Another object of the present invention is to provide a complete sterilization of the tissue affected by ischemic skin ulcer using plasma treatment.

Another objective of the present invention is to simultaneously provide both restoration of blood flow and sterilization ischemic to tissue affected by ischemic skin ulcer for effective healing.

Another objective of the present invention is to use a self-standing plasma discharge device without the use of patient body as a second electrode.

A method according to the present invention includes the generation of plasma discharge near ischemic skin ulcer within 2 cm without the need of a long hose for the transport of NO gas in the aforementioned "Plazon" discharge system.

Another method according to the present invention is to provide a plasma discharge system, where hot plasma discharge species cool to room temperature by diffusive expansion at the nozzle of the discharge system without a separate cooling method.

Another method according to the present invention is to provide a plasma discharge system, where hot plasma discharge species cool to room temperature by diffusive expansion at the nozzle of the discharge system within 2 cm space.

Another method according to the present invention includes a production of arc discharge near the exit of the plasma discharge system so that the other plasma species such as UV, singlet oxygen, hydrogen peroxide, etc. can effectively participate in the plasma treatment of the skin ulcer via sterilization of wounded skin.

Methods according to the present invention for treating a skin ulcer using non-thermal plasma include flowing a gas through a cold spark discharge zone simultaneously with the creation of a pulsed spark discharge to give rise to a non-thermal plasma emitted from a conduit, the non-thermal plasma comprising NO; and contacting a skin ulcer with said non-thermal plasma for sufficient time and intensity to give rise to treatment of the skin ulcer.

Methods according to the present invention for treating a skin ulcer also include flowing gas through a conduit capable of fluidically communicating a gas, a plasma, or both, therethrough, a portion of the conduit capable of being connected to a gas supply, and a second portion of the conduit capable of emitting a plasma, the conduit comprising therewithin: a positive electrode comprising a sharp tip, the positive electrode capable of receiving a high voltage from a positive terminal of a high voltage power supply; a ground plate electrode comprising an opening passing through the plate, the opening characterized as having a dimension, d, the ground plate electrode capable of being in electrical communication with ground and a negative electrode of said high voltage power supply, the sharp tip of the positive electrode located proximate to the opening of the ground plate electrode by distance h, the distance h defining a spark zone between the sharp tip of the positive electrode and the opening of the ground plate electrode; wherein the sharp tip of the positive electrode, the opening of the ground plate electrode and the spark zone are located within the second portion of the conduit capable of emitting a plasma; and repeatedly charging and discharging a capacitative circuit electrically coupled to a high voltage power supply to provide a voltage of at least 500 V across the positive and ground negative to give rise to a pulsed spark discharge at a rate of at least 1 Hz in the spark zone; flowing a gas through the spark zone simultaneously with the creation of the pulsed spark discharge to give rise to a non-thermal plasma emitted from the second portion of the conduit, the non-thermal plasma comprising NO; and contacting a skin ulcer with said non-thermal plasma for sufficient time and intensity to give rise to treatment of the skin ulcer.

Other features and advantages of the present invention will become apparent from the following description of the invention which refers to the accompanying drawings.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there is shown in the drawings embodiments that are presently preferred, it being understood, however, that the invention is not limited to the specific instrumentalities disclosed. The drawings are not necessarily drawn to scale. In the drawings.

DETAILED DESCRIPTION OF ILLUSTRATIVE EMBODIMENTS

Figure 1:
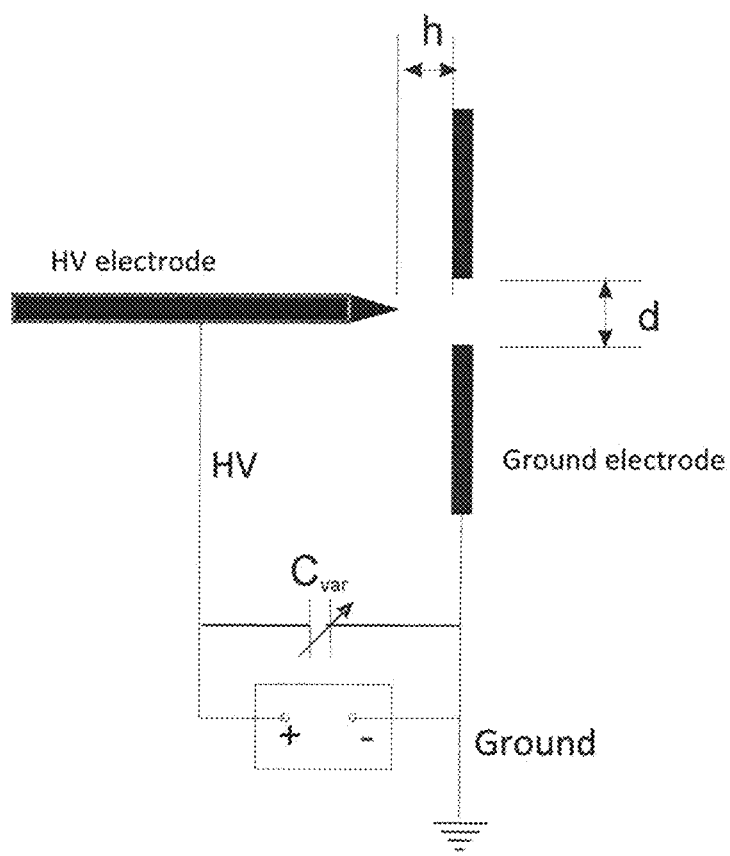
FIG. 1 illustrates a sketch of a device to produce atmospheric pressure pin-to-hole spark discharge.

The present subject matter may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Plasmas, referred to as the "fourth state of matter," are partially ionized gases with a certain number of electrons that are not bound to atoms or molecules. In recent years, plasmas have become of significant interest to researchers in fields such as organic and polymer chemistry, fuel conversion, hydrogen production, environmental chemistry, biology, and medicine, among others. This is, in part, because plasmas offer several advantages over traditional chemical processes. For example, plasmas can generate much higher temperatures and energy densities than conventional chemical technologies; plasmas are able to produce very high concentrations of energetic and chemically active species; and plasma systems can operate far from thermodynamic equilibrium, providing extremely high concentrations of chemically active species while having gas temperature as low as room temperature. Many details concerning the generation and applications of plasmas are described in PLASMA CHEMISTRY (2008), by Fridman.

Plasmas are generated by ionizing gases using any of a variety of ionization sources. Depending upon the ionization source and the extent of ionization, plasmas may be characterized as either thermal or non-thermal. Thermal and non-thermal plasmas can also be characterized by the temperature of their components. Thermal plasmas are in a state of thermal equilibrium, that is, the temperature of the free electrons, ions, and heavy neutral atoms are approximately the same. Non-thermal plasmas, or cold plasmas, are far from a state of thermal equilibrium; the temperature of the free electrons is much greater than the temperature of the ions and heavy neutral atoms within the plasma.

The initial generation of free electrons may vary depending upon the ionization source. With respect to both thermal and non-thermal ionization sources, electrons may be generated at the surface of the cathode due to a potential applied across the electrode. In addition, thermal plasma ionization sources may also generate electrons at the surface of a cathode as a result of the high temperature of the cathode (thermionic emissions) or high electric fields near the surface of the cathode (field emissions).

The energy from these free electrons may be transferred to additional plasma components, providing energy for additional ionization, excitation, dissociation, etc. With respect to non-thermal plasmas, the ionization process typically occurs by direct ionization through electron impact. Direct ionization occurs when an electron of high energy interacts with a valence electron of a neutral atom or molecule. If the energy of the electron is greater than the ionization potential of the valence electron, the valence electron escapes the electron cloud of the atom or molecule and becomes a free electron according to:

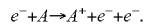

$$e^- + A \rightarrow A^+ + e^- + e^-.$$

As the charge of the ion increases, the energy required to remove an additional electron also increases. Thus, the energy required to remove an additional electron from $A^+$ is greater than the energy required to remove the first electron from A to form $A^+$. A benefit of non-thermal plasmas is that because complete ionization does not occur, the power of the ionization source can be adjusted to increase or decrease ionization. This ability to adjust the ionization of the gas provides for a user to "tune" the plasma to their specific needs.

An exemplary thermal plasma ionization source is an arc discharge. Arc discharges have been otherwise used for applications such as metallurgy, metal welding and metal cutting and are known per se. Arc discharges are formed by the application of a potential to a cathode. Arc discharges are characterized by high current densities and low voltage drops. Factors relevant to these characteristics are the usually short distance between the electrodes (typically a few millimeters) and the mostly inert materials of the electrodes (typically, carbon, tungsten, zirconium, silver, etc). The majority of electrons generated in arc discharges are formed by intensive thermionic and field emissions at the surface of the cathode. That is, a much larger number of the electrons are generated directly from the cathode as opposed to secondary sources such as excited atoms or ions. Because of this intense generation of electrons at the cathode, current at the cathode is high, which leads to Joule heating and increased temperatures of the cathodes. Such high temperatures can result in evaporation and erosion of the cathode. The anode in arc discharges may be either an electrode having a composition identical or similar to the cathode or it may be another conductive material. For example, the anode in arc discharges used in metal welding or cutting is the actual metal be welded or cut. Typical values for parameters of thermal arc discharges can be seen in Table 1:

TABLE 1

Arc Discharge Parameters

| Parameters of a Thermal Arc Discharge | Typical Values |
|---|---|
| Gas Pressure | 0.1 to 100 atm |
| Arc Current | 30A to 30 kA |
| Cathode Current Density | $10^4$ to $10^7$ A/cm$^2$ |
| Voltage | 10 to 100 V |
| Power per unit length | 1 to 10 kW/cm |
| Electron Density | $10^{15}$ to $10^{19}$ cm$^{-3}$ |
| Gas Temperature | 1 to 10 eV |
| Electron Temperature | 1 to 10 eV |

Although thermal plasmas are capable of delivering extremely high powers, they have several drawbacks. In addition to the electrode erosion problems discussed above, thermal plasmas do not allow for adjusting the amount of ionization, they operate at extremely high temperatures, and they lack efficiency.

Non-thermal plasma ionization sources have alleviated some of the above-mentioned problems. Exemplary ionization sources for non-thermal plasmas include glow discharges, gliding arc discharges, and floating electrode dielectric barrier discharges, among others. In contrast to thermal plasmas, non-thermal plasmas provide for high selectivity, high energy efficiencies, and low operating temperatures. In many non-thermal plasma systems, electron temperatures are about 10,000 K while the bulk gas temperature may be as low as room temperature.

Dielectric barrier discharge plasmas (DBD) may be generated using an alternating voltage at frequencies ranging from about 0.5 kHz to about 500 kHz between a high voltage electrode and a ground electrode. In addition, one or more dielectric barriers are placed between the electrodes. DBD occurs at atmospheric pressure in air or other gases when sufficiently high voltage of sinusoidal waveforms or short duration pulses are applied between two electrodes, with at least one of the electrodes being insulated. DBDs have been employed for over a century and have been used for the generation of ozone in the purification of water, polymer treatment (to promote wettability, printability, adhesion), and for pollution control. DBDs prevent spark formation by limiting current between the electrodes.

Several materials can be utilized as the dielectric barrier. These include glass, quartz, and ceramics, among others. The clearance between the discharge gaps typically ranges from about 0.1 mm and several centimeters. The required voltage applied to the high voltage electrode varies depending upon the pressure and the clearance between the discharge gaps. For a DBD at atmospheric pressure and a few millimeters between the gaps, the voltage required to generate a plasma is typically about 10 kV. The insulator between the electrodes prevents the build-up of high current. As a result, the discharge creates electrically safe plasma without substantial gas heating.

Non-thermal atmospheric pressure dielectric barrier discharge plasma has emerged as a novel tool in medicine. This non-thermal plasma enables many new medical applications including living tissue sterilization, blood coagulation, apoptosis induction in malignant cells, cell attachment modulation, and wound healing, among others.

Another application of plasma treatment is for skin cancer, where living tissue itself is used as one of the electrodes and directly participates in the active plasma discharge processes, providing direct plasma treatment (for sterilization) of skin. Dielectric Barrier Discharge (DBD) method is used to generate plasma between the quartz-surface covered high-voltage electrode and the patient's skin which serves as a second electrode. Direct application of the high-voltage (10-40 kV) non-thermal plasma discharges in atmospheric air is used to treat skin cancer in patients. Since the DBD method utilizes human body as the second electrode, discharge current in the DBD is limited below the values permitted for treatment of living tissue.

An exemplary disorder may be various skin ulcers, with their treatment using a plasma discharge, which simultaneously provides vasodilation and the sterilization of epidermis.

Three types of skin ulcers are known. The first is an acute skin ulcer caused by burn. The second is a chronic skin ulcer caused by diabetes. The third is a chronic skin ulcer caused by pressure.

A burn injury, a very painful injury, can be caused by a number of sources, which include thermal, chemical, electrical, light, and radiation. Every year, thousands die in America as a result of burns, the treatment for which often requires long-term hospitalization. Burn injury is one of the leading causes of unintentional death in the United States.

Burn injuries can affect muscles, bones, nerves, and blood vessels. Since burns injure the skin, they impair the body's normal fluid/electrolyte balance and blood supply to the injured skin area. In particular, the blood vessels underneath the burn injury constrict, reducing the supply of oxygen, which is needed for the cell survival in and around the burn injury.

Another form of skin ulcer in this invention is diabetic ulcer. The most common risk factors for ulcer formation in diabetes include diabetic neuropathy and peripheral arterial occlusive disease, both of which reduce blood supply to the areas affected by the ulcer.

Diabetic foot ulcer is one of the most common foot injuries leading to lower extremity amputation in the industrialized world. The risk of lower extremity amputation is 30 times higher in diabetics than in persons who do not have diabetes mellitus. Furthermore, foot complications are the most frequent reason for hospitalization in patients with diabetes, accounting for up to 25 percent of all diabetic admissions in the United States and Great Britain.

The vast majority of diabetic foot complications resulting in amputation begin with the formation of skin ulcers. Early detection and appropriate treatment of these ulcers may prevent up to 85 percent of amputations. Indeed, one of the disease prevention objectives outlined in the "Healthy People 2000" project of the U.S. Department of Health and Human Services is a 40 percent reduction in the amputation rate for diabetic patients.

Peripheral arterial occlusive disease is four times more prevalent in diabetics than in nondiabetics, indicating that the blood supply might have been impaired among them. The arterial occlusion typically involves the tibial and peroneal arteries. Patients with diabetic skin ulcer have clear clinical signs of ischemia particularly in the lower extremity. Various noninvasive vascular tests or imaging studies can demonstrate that the patient has peripheral arterial occlusive disease.

Signs of peripheral arterial disease (PAD) include claudication, pain occurring in the lower extremities at rest or during the night, and reduced ankle-brachial index (ABI), all of which indicate the insufficient blood supply. Note that ABI is determined by the ankle systolic pressure divided by the brachial systolic pressure. Peripheral artery disease is a form of vascular disease, wherein arterial occlusions effect a reduction in blood flow and perfusion. The peripheral arterial disease is the origin of approximately 340,000 lower limb amputations per year in the industrial world.

A common method of treatment for the diabetic skin ulcer is to restore adequate tissue perfusion, which can be accomplished by possible revascularization such as bypass surgery or stent insertion if arterial occlusions are focal. However, if the arterial blockages are of diffuse nature, the only option to restore blood flow is the use of medications such as anti-platelet drugs (Aspirin and Platal), vasodilators, lipid-lowering statin derivatives, and anti oxidants (vitamin B and C).

A pressure ulcer is another type of skin wound caused by the weight of own body as a patient stays in one position for too long without shifting weight. This often takes place when a patient is bedridden. The constant pressure against the skin reduces the blood supply to that area so that the capillary blood vessels are compressed by the pressure, producing a ischemic condition around the tissue perfused by the capillaries. When the external pressure by the body weight is greater than the hydrostatic capillary pressure or osmotic pressure over an extended period of time, then the ischemic condition gets worse. Subsequently, the permeability of the capillary vessel wall adversely alters, resulting in the inflammation and necrosis of cells in the surrounding muscle tissues. In short, the affected tissue by burn injury dies due to insufficient oxygen supply.

Prognosis of a pressure ulcer is excellent for early-stage ulcers. However, neglected and late-stage ulcers pose risk of serious infection and are difficult to heal. An estimated 1.3 to 3 million patients in the US have pressure ulcers; incidence is highest in older patients, especially when hospitalized or in long-term care facilities. Aging increases risk, in part because of reduced subcutaneous fat and decreased capillary blood flow.

European Patent EP1803464 discloses an external agent for treatment of skin ulcer which has an excellent healing effect on intractable skin ulcer such as bedsore, diabetic skin ulcer and ischemic skin ulcer. The agent is characterized in that it comprises a composition containing at least one selected from the group consisting of granulocyte colony stimulating factor (G-CSF), stromal cell-derived factor-1 (SDF-1) and CD41-positive cells, and a hydrophilic high molecular substance.

Effective use of plasma in surgery has been first demonstrated in 1960s: plasma afterglow jet of an inert gas has been applied for tissue sectioning with instant blood coagulation. Typical plasma-surgical devices are referred to as "plasma scalpels".

The Nobel Prize in medicine and biology was awarded in 1998 to R. F. Furchgott, L. J. Ignarro, and F. Murad for their work in investigation of function of nitrogen oxide ("NO") as a signal molecule. Today it is well known that in a human organism, NO serves a multitude of essential biological functions—it regulates blood vessel tone (via relaxation of flat epithelial cells) and blood coagulation, immune system and early apoptosis, neural communication and memory, relaxation of flat bronchial and gastrointestinal muscles, hormonal and sex functions, NO offers antimicrobial and antitumor defense, etc. In pathology, NO plays a major role in adaptation, stress, tumor growth, immunodeficiency, cardiovascular, liver, and gastrointestinal tract disease, etc. This explains wide possibilities of the plasma-generated exogenic NO in multiple medical applications.

Importance of exogenic NO in infection and inflammation processes is also well studied and is linked with antimicrobial effects; stimulation of macrophages; induction of cytokines, T-lymphocytes, and many immunoglobulins; interaction with oxygen radicals; and influence on microcirculation, cytotoxic and cytoprotective role in different conditions. During inflammation, macrophages and some other cells (i.e. aibroblasts, epithelial cells, etc.) produce NO via inducible NO-synthase (iNOS) in quantities significantly greater (2 orders of magnitude) than normal when NO is formed via constructional NOS: endothelial (eNOS) and neuronal (nNOS).

Exogenic NO is also crucial in trauma wound processes. Activity of inducible NO-synthase (iNOS) grows substantially in trauma wounds, burn wound tissues, bone fracture site tissues, and others in the inflammatory and proliferation phases of the healing process. Activation of iNOS was also discovered in cultivation of wound fibroblasts. Macrophage activation in a wound, cytokine synthesis and proliferation of fibroblasts, epithelization and wound healing processes are all linked with the activity levels of iNOS. In animal models, injection of iNOS inhibitors disrupts all of these processes and especially the synthesis of collagen, while NO synthesis promoters increase the rate of these processes.

Animals with iNOS deficiency demonstrate significant decrease in wound healing rate, however this can be reversed by injection of iNOS gene. In complicated wound models, for example in experimentally-induced diabetes, protein deficiency, injection of corticosteroids or immuno-suppressants, and also in patients with tropic ulcers, lowered activity of iNOS is usually discovered which correlates to slowed healing processes. Exogenic delivery of NO-donors (nitrogen-containing compounds) to the wound promotes and speeds up healing processes in animals with complicated wounds and in animals with inhibited iNOS.

EPR spectroscopy was utilized to investigate the dynamics of level of endogenic and exogenic NO in wound tissues and in organs in an animal model (70 rats). NO "trap", diethylthiocarbamate (DETC), was injected into rats with a full thickness flat wound of 300 mm$^2$ area five days prior to EPR analysis. Following euthanasia, the samples were collected from the animals: blood, granular tissue from the bottom of the wound and from internal organs (heart, liver, kidney, and the small intestine). For a portion of the animals, on the 5$^{th}$ day following the initial wound introduction, the wound surface was treated by the NO-containing gas flow (500 ppm). Without the NO treatment, the results indicate high content of endogenic NO in wound tissues (10.3±2.3 μM). The liver of the animals with the wound contained 2.3±1.4 μM of DETC-ironmononitrosyl complex (IMNC); while the control group (without the wound)—only 0.06±0.002 μM.

Animals without the wound were used for investigation of penetration capability of gaseous exogenic NO through undamaged tissues of abdominal wall. Treatment by NO-containing gas flow was performed for 60 and 180 seconds. A nearly linear dependence of the amount of DETC-IMNC produced in the liver and blood of the animal on the NO-containing gas treatment time was observed. Two minutes following the 180 second treatment a maximum signal was registered in the bowels of the animal—2.6 times higher than in the control group. In the heart, liver, and kidney the difference was 1.7 times. These results are indicative of the ability of the exogenic NO molecules to penetrate the undamaged tissues.

A more complex relationship was observed in treatment by exogenic NO of the wound tissues. If the animal was euthanized 30-40 minutes following the treatment, then NO content in wound tissue and blood was observed to raise 9-11 times more than in the case of the 2-minute interval. This is probably due to formation of peroxinitrite, which can be formed through NO reacting with superoxide anions ($O_2^-$), as it is known that the superoxide levels are increased in the organism during the inflammatory processes. In response to the oxidative stress, the organism mobilizes the antioxidant defense mechanisms first via the increase in the levels of reducing agents (thioles, ascorbate, etc.), and then via activation of synthesis of antioxidant enzymes. Thirty to fourty minutes following the wound treatment by exogenic NO, activation of the first cascade of antioxidant defense allowed for significant decrease in the level of superoxide anions. This considerably decreases its destructive influence on DETC-IMNC and the nitrosyl complexes of the hemoproteins, which leads to the increase in their concentration as is detected by the EPR spectroscopy. Additionally, activation of NOS by the increase in endogenic NO cannot be neglected. It partially explains the discovered phenomena of stimulation of wound development processes via the influence of exogenic NO, when there is a deficiency of endogenic NO or excess of free radicals, including superoxide.

In experiments on the cornea of rabbits, the mucous membrane of the cavity of the mouth of hamsters, and on the meninx membrane of rats, via lifetime biomicroscopy it was found that the effect of the expansion of the opening of the micro-vessels under the influence of exogenic NO (500 ppm) lasts with varying intensity up to 10-12 hours, while the lifetime of NO molecules is no more than 10-15 seconds. The experiments serve as additional evidence that single application of exogenic NO initiates a cycle of cascade reactions, including biosysnthesis endogenic NO, which leads to a long-lasting effect and explains the successes of the NO therapy.

Action of the exogenic NO on the cellular cultures of the human fibroblasts and rat nervous cells was studied by researchers. Single treatment by the plasma-generated NO of the cell cultures significantly increases (2.5 times) the cell proliferation rate via the increase of DNA synthesis (tested by inclusion of $C^{14}$ thymidine) and to a lesser extent (1.5 times) increase of protein synthesis by the cells (tested by inclusion of $C^{14}$ aminoacids). As expected, the stimulating effect is dose-dependent. The action of exogenic NO on the phagocytic activity of the cultured wound macrophages from the washings of the trophic human ulcers, studied by the photochemiluminescence revealed that a maximum increase in the luminous intensity (1.95 times in comparison with control) testifies about the activation of the proteolytic enzymes of macrophages under the effect of NO-CGF. Statistically significant increase in fluorescence of macrophages was observed in less than 24 hours following a 30-second treatment.

In vitro investigation of the influence of NO-CGF on *Escherichia coli, Staphylococcus aureus, Pseudomonas aeruginosa, Proteus vulgaris*, and *Candida albicans*, which are typically associated with many hospital infections, showed that 75 sec of treatment by NO-CGF significantly decreases viable colony forming units, 80 seconds practically removes them all, and no growth is detected at all following 90 seconds of treatment.

Application of air plasma and exogenic NO in the treatment of the trophic ulcers of the vascular etiology in 318 patients showed high efficiency of NO-therapy in the treatment of the venous and arterial trophic ulcers of lower extremities with an area of from 6 to 200 cm² [21, 94]. For assessment of the effectiveness of the plasma NO-therapy, clinical and planimetric indices were analyzed in the course of the process of sanitation and epithelization of ulcers, a bacteriological study of discharge from the ulcer, cytological study of exudate, a histopathological study of biopsies from the boundary of a trophic ulcer, the indices of microcirculation (according to the data obtained by Laser Doppler Flowmetry—LDF) and transcutaneous partial pressure of oxygen ($pO_2$). In the main groups of observations trophic ulcers were processed in the regime NO-therapy (500 and 300 ppm); or prior to beginning the therapy the ulcer surface was treated in the regime of coagulation until the evaporation of necrotic debris. Following initial treatment, the wounds were treated for 10-30 days in the NO-therapy regime. In the control group proteolytic and antimicrobial drugs were used—in the phase of exudation and necrosis, and wound coatings—in the phase of tissue regeneration and epithelization.

Using the plasma-generated NO for local treatment of ulcerous and necrotic tissues in patients with diabetes (diabetic foot ulcer) has been demonstrated. Patients were selected for this study following two months of unsuccessful treatments by the state-of-the-art techniques. Already from the first few sessions the difference was evident: inflammatory reaction was clearly reduced, patients reported decrease in pain, and cleansing of the ulcer surface was clearly visible. Following 10 sessions, most patients expressed positive healing dynamics: ulcer size decreased to ⅓-¼ of the original size. LDF markers, $pO_2$, and bacteriological investigation all showed a positive dynamic. In patients with relatively small-sized ulcers (initial diameter less than 1 cm) full epithelization occurred by 6-8 NO-treatment sessions. Period of stationary treatment and full clinical recovery of patients was noticeably shortened (on average by 2.3 times). In the cases of large ulcerating wounds, the necessity for amputation decreased 1.9 times.

Effectiveness of the exogenic NO and air plasma on healing of the pyoinflammatory diseases of soft tissues has been demonstrated studying 520 patients with the purulent wounds of different etiology and 104 patients with the phlegmonous-necrotic form of the erysipelatous inflammation. By the $5^{th}$ day of therapy wounds on most of the patients in the experimental group (90%), contrary to the control group, were clear of necrotic tissue, and the wounds began to be covered by bright spots of granular tissue. Microbial infestation of the wound tissue had lowered from $10^{6-8}$ colony forming units (cfu) per gram of tissue to $10^{1-2}$. Data from complex analysis of microcirculation (LDF, $pO_2$) showed significant repair of the microvasculature and blood flow in the wound tissues in most of the patients in the experimental group. The predominant types of cytograms were regenerative and regenerative-inflammatory with a notable increase in fibroblast proliferation—on average 18.5±3.1%. Notable morphological changes in the biopsies were the significant development and maturing of the granular tissue and the regeneration of epithelial tissue at the edges. Large suppurated wounds, for example suppurated burn wounds, by day 7-10 of treatment were clear of the pyonecrotic exudate and were beginning to be covered by granular tissue, in other words these wounds were ready for dermautoplasty.

Effectiveness of the plasma NO-therapy is most apparent with the treatment of the pyonecrotic form of erysipelatous inflammation—patients who are considered the most severe cases of the purulent surgery departments. The combination of surgical preparation of extensive pyonecrotic centers and local NO-therapy allowed in the majority of the patients with phlegmonous-necrotic erysipelas during 12-14 days of treatment to liquidate heavy pyonecrotic process and to create conditions for completion of reparative procedures.

Significant advancement in the plasma surgery, wound healing and tissue regeneration is due to development of the "Plazon" system based on the jet of hot air plasma rapidly quenched and providing relatively high NO concentration with significant therapeutic effect. This plasma device is used in two modes. In the first "hot mode" plasma jet is used for rapid coagulation and sterilization of wound surfaces, destruction and desiccation of dead tissue and pathologic growths, dissection of biological tissues. In the second "cold mode" NO-containing plasma gas flow with temperature of 20 to 40° C. is used for stimulation of regenerative processes and wound healing. The "Plazon" generators are the DC arcs with different configurations of the exit channels corresponding to the different applications (blood coagulation, tissue destruction, therapeutic manipulation/stimulation). Main and common elements of the system construction are the liquid-cooled cathode, intra-electrode insert, and anode. Atmospheric air enters the manipulator through the built-in micro-compressor, passes through the plasma arc, heats up and thus accelerates, and exits through the hole in the anode of the plasma-generating module. Plasma temperature at the anode exit varies depending on configurations of a device, corresponding to specific medical applications. Further away from the anode, temperature drops rapidly, and at 30-50 mm from the anode, the flow is composed simply of the warm gas, and the plasma-generated NO.

Nitrogen oxide content in the gas flow is mainly determined by the quenching rate. The necessary quenching rate for effective operation of the medical device is about ~$10^7$-$10^8$K/sec. Commonly, the cooling rate of plasma jets is on the order of ~$10^6$ K/sec. Thus, to achieve the cooling rate of ~$10^7$-$10^8$ K/sec, it is necessary to utilize additional cooling of the plasma jet, which has been achieved by special construction of the plasma nozzles.

The therapeutic manipulator-stimulator configuration of the "Plazon" discharge system is used solely for therapeutic treatment by exogenic nitrogen oxide. The principle difference of this manipulator is that the air-plasma jet does not freely exit into the atmosphere, but rather it exits the anode into the two-step cooling system, gas channels of which are created in a maze scheme to force-cool the jet by the liquid circulating from the cooling system. This construction allows one to obtain NO-containing gas flow (NO-CGF) with sufficiently low temperature, and optimal concentration of nitrogen oxide molecules, which makes it possible to apply this manipulator for treatment of external body surfaces by using the cooling hose of 150 mm length (temperature of NO-CGF at the exit ~36° C.). Unfortunately, NO content in the gas flow exponentially decreases with the distance from the exit channel, which is one of the drawbacks of the device and method. Accordingly, there is a continuing need to improve the methods and devices for synthesizing NO-CGF that have moderate temperatures and which can be used in biomedical applications.

Another application of plasma treatment is for skin cancer, where living tissue itself is used as one of the electrodes and directly participates in the active plasma discharge processes, providing direct plasma treatment (for sterilization) of skin. Dielectric Barrier Discharge (DBD) plasma is generated in this case between the quartz-surface covered high-voltage electrode and the patient's skin which serves as a second electrode.

Direct application of the high-voltage (10-40 kV) non-thermal plasma discharges in atmospheric air is used to treat skin cancer in patients. Due to safety and guaranteed non-damaging regimes, discharge current is limited below the values permitted for treatment of living tissue. Moreover, discharge itself should be homogeneous enough to avoid local damage and discomfort.

Fridman et al. developed the floating-electrode dielectric barrier discharge (FE-DBD), which operates under the conditions where one of the electrodes is a dielectric-protected powered electrode and the second active electrode is a human skin. In the FE-DBD setup, the second electrode (a human, for example) is not grounded and remains at a floating potential. Discharge ignites when the powered electrode approaches the surface to be treated at a distance (discharge gap) less than about 3 mm, depending on the form, duration, and polarity of the driving voltage.

FIG. 1 shows the basic concept of the present invention to produce atmospheric pressure pin-to-hole spark discharge (PHSD). PHSD is ignited in the pin-to-hole electrode configuration utilizing two electrodes. One electrode has a sharp pin-shape at the tip and is powered from a positive high voltage (HV) output of a power supply, whereas the other electrode, Ground Electrode, is grounded and made of a circular plate with an opening at the center for the release of PHSD. The HV electrode is aligned to the center of the opening of the ground plate electrode.

Figure 2:
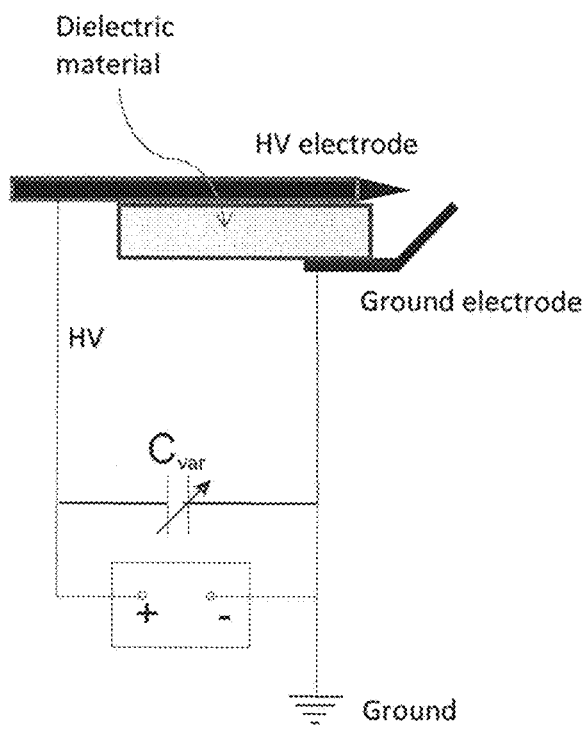
FIG. 2 illustrates a sketch of an alternative device to produce atmospheric pressure pin-to-hole spark discharge.

FIG. 2 shows an alternative concept of the present invention where two wires are utilized. The HV electrode has a sharp tip, and the other wire electrode is grounded. There is a dielectric material between the two electrodes such that the breakdown takes place between the tip of the HV electrode and the end of the ground wire electrode.

In order to produce pulses a capacitor is connected in parallel to electrodes from the electric circuit point of view. The typical size of the capacitor can be in the range of from about 0.01 µF to about 1 µF.

If the voltage between the two electrodes is high enough for breakdown to occur, dense hot spark plasma is generated. For example, for the case shown in FIG. 1, where "h" is approximately 1-3 mm and "d" is approximately 2-3 mm, a suitable voltage to be applied is about 0.5-5 kV, which is large enough to produce the breakdown between the tip of the HV electrode and the edge of the outer aperture of Ground electrode. In this case, the discharge energy varies from 0.1 to 6 J per pulse.

When the breakdown occurs, a short pulse discharge will be formed between the two electrodes with high temperature of several thousand degree K. As a result of the sudden increase in temperature, there will be a sudden increase in the pressure of the plasma discharge. Due to the increased pressure, the plasma discharge expands outward from the tip of HV electrode through the aperture characterized as "d". Since "d" represents the hole in the Ground electrode in FIG. 1, the plasma discharge will exit through the opening in the Ground electrode. Subsequently, the expanding plasma discharge propagates outside of the hole in the Ground electrode, resulting in a rapid cooling of the discharge.

In the present invention, a spark is produced intermittently, i.e., pulsed spark. The pulse duration is several micro seconds, at least 2, or at least 5, or at least 10, or at least 20, or even at least 100 microseconds with a pulse frequency of typically at least 1 Hz, or even at least 2, 4, 8, or even at least 10 Hz.

FIG. 2 illustrates an alternative plasma discharge using two wire electrodes separated by a dielectric material. The electrode closer to the human body is used as a ground electrode.

Figure 3:
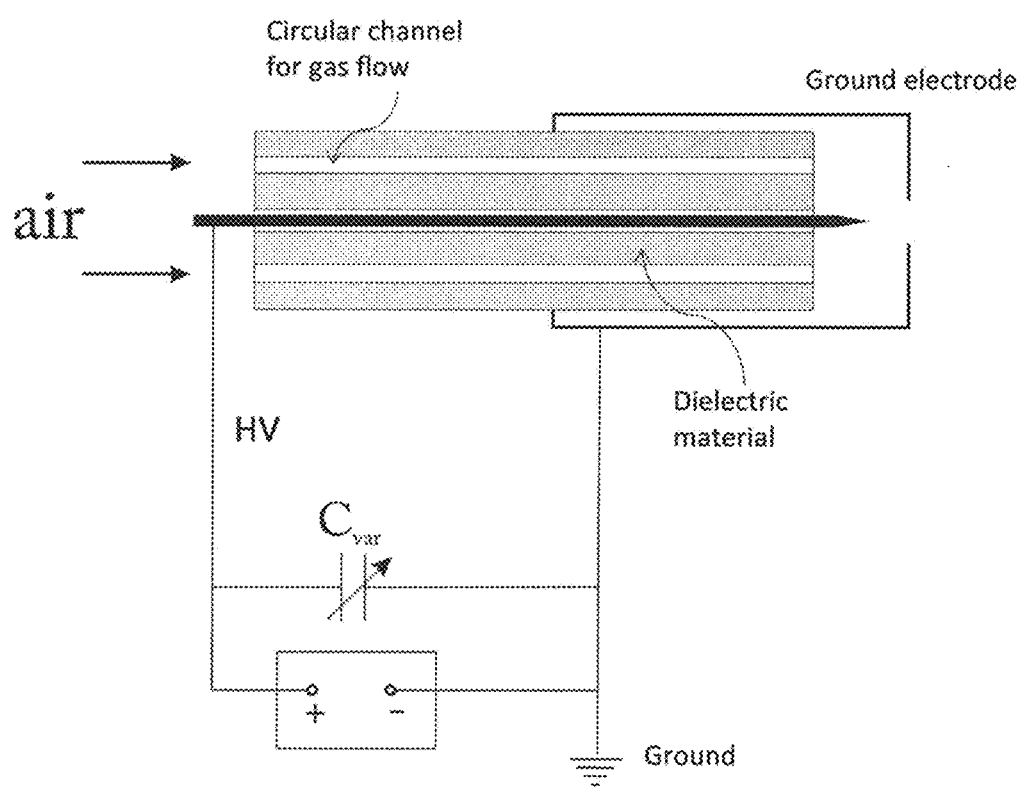
FIG. 3 illustrates a sketch of an alternative device to produce atmospheric pressure pin-to-hole spark discharge operating at a high frequency assisted by air flow.

The present invention can utilize a pulse spark at a high frequency, for example, 10-30 Hz. In this case, the present invention uses gas flow to assist the cooling of plasma discharge as shown in FIG. 3. The HV electrode is positioned at the center of the co-axial configuration, whereas the outer circular tubular case or other suitable conduit is used as a ground electrode. In this case, the two electrodes are constructed in a co-axial configuration as shown in FIG. 3, where a dielectric material is used to cover the HV electrode except for the end tip area. At the center of the dielectric material, a hole is made for the installation of the HV electrode. Another hole (or two holes as shown in FIG. 3) will be made and used for the injection of gas flow.

In some embodiments, an atmospheric pressure pin-to-hole spark discharge is produced using a device without the use of cooling gas flow in the present invention. In such embodiments, the plasma discharge exits from a hole in a circular plate geometry and appears as a regular light.

The plasma discharge produced from the device in the present invention is cold and thus safely applied to the human body, even without the use of cooling gas flow.

Figure 4:
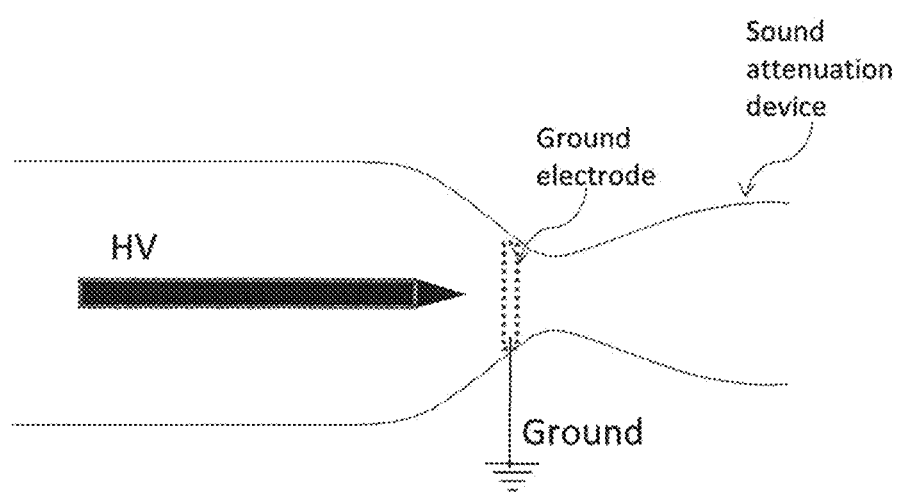
FIG. 4 shows a sound attenuation device at the end of atmospheric pressure pin-to-hole spark discharge.

The pulse discharge produces a relatively large bang sound due to sudden expansion of pressure around the electrode tip. Hence, it is desirable to reduce the sound level to provide a comfort feeling to patients. FIG. 4 shows a sound attenuation device in a form of a diffuser or muffler, which is attached at the exit of plasma discharge device.

Figure 5:
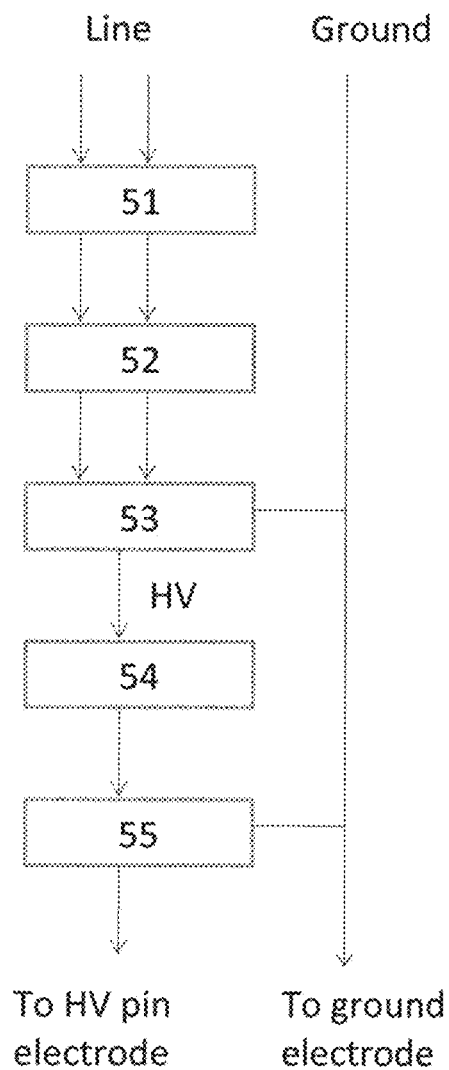
FIG. 5 shows a block diagram of the pulse discharge.

FIG. 5 shows a block diagram of the pulse discharge. A ballast 51 is used to limit current. A signal generator 52 is used to produce a sinusoidal or pulse wave. Then, a high voltage transformer 53 is used to increase the input voltage of 110 V to a high voltage of 10,000 to 30,000 V. A rectifier 54 and a pulse forming device 55 such as a spark gap, capacitor, FID (fast ionization device), SOS (semiconductor open switch) are used to generate a pulse discharge.

Figure 6:
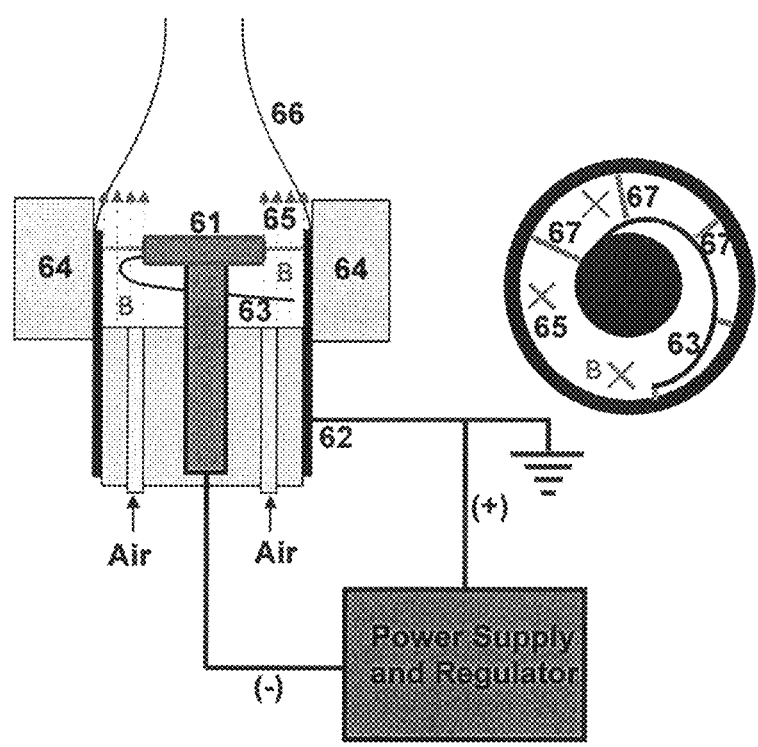
FIG. 6 shows a sketch of an alternative device of a magnetically driven gliding arc discharge.

FIG. 6 shows a sketch of an alternative device of a magnetically driven gliding arc discharge. An arc is formed between a center high voltage electrode 61 and the outer ring electrode which is grounded. In particular, a spiral wire 63 is protruded from the center HV electrode 61 to assist the formation of arc 66 between the two electrodes. The temperature of the arc is relatively high so that if the arc stays in one location, it could burn the metal part. The current invention utilizes a magnet field 55 produced by permanent ring magnets 64 to rotate the arc along the circumferential direction according to the Lorentz law. Note that the magnetic field is axially oriented. The movement of the arc 67 as a function of time is shown in the cut-away view as four straight lines 67 between the HV center electrode and the outer ring electrode. The strength of the permanent magnet is 0.1 Tesla, the current is 10-100 mA, the voltage is 2,000-5,000 V, and the frequency is in a range of 50 to 200 Hz. A nozzle shaped outlet channel on a suitable conduit is used to direct the plasma species generated from the magnetically driven plasma discharge to human skin.

Figure 7:
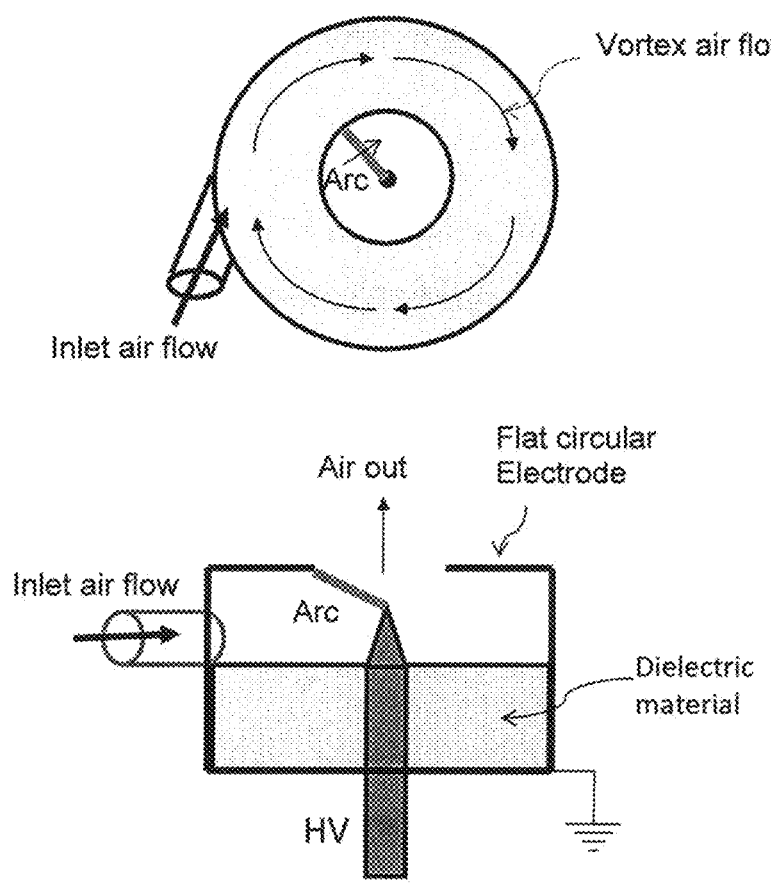
FIG. 7 shows a sketch of an alternative device of a gliding arc driven by a vortex flow.

FIG. 7 shows a sketch of an alternative device of a gliding arc driven by a vortex flow. The purpose of the gliding arc is to move the high-temperature arc around the perimeter of the outer ring electrode. In order to generate a strong vortex flow, a compressed air enters a suitable conduit tangentially along the wall of the outer ring electrode. A vortex flow is shown in the top figure in FIG. 7. An arc is formed between the center HV electrode and the edge of the ground electrode, which is indicated as a flat circular electrode. The arc continues to move along the edge of the flat circular electrode as it is pushed by a strong vortex flow.

Accordingly, suitable methods of treating a skin ulcer using non-thermal plasma, include the steps of flowing a gas through a cold spark discharge zone simultaneously with the creation of a pulsed spark discharge to give rise to a non-thermal plasma emitted from a conduit, the non-thermal plasma comprising NO. A skin ulcer can then be contacted with the non-thermal plasma containing NO for sufficient time and intensity to give rise to treatment of the skin ulcer. In some embodiments it is desirable that the cold spark discharge voltage is in the range of from about 500 V to about 5 kV. The diameter of the non-thermal plasma is suitably in the range of from about 3 mm to about 5 mm. A suitable pulsed spark discharge is pulsed at a frequency in the range of from about 1 Hz to about 7 Hz. The duration of the pulsed spark discharge can be in the range of from about 5 microseconds to 50 microseconds. Each pulsed spark discharge is characterized as having an energy per pulse in the range of from about 0.1 J to about 2 J.

Describing in further detail, some methods of treating a skin ulcer using non-thermal plasma, include the steps of flowing gas through a conduit capable of fluidically communicating a gas, a plasma, or both, therethrough, a portion of the conduit capable of being connected to a gas supply, and a second portion of the conduit capable of emitting a plasma. A suitable conduit can include therewithin: a positive electrode comprising a sharp tip, the positive electrode capable of receiving a high voltage from a positive terminal of a high voltage power supply; a ground plate electrode comprising an opening passing through the plate, the opening characterized as having a dimension, d, the ground plate electrode capable of being in electrical communication with ground and a negative electrode of said high voltage power supply, the sharp tip of the positive electrode located proximate to the opening of the ground plate electrode by distance h, the distance h defining a spark zone between the sharp tip of the positive electrode and the opening of the ground plate electrode. The sharp tip of the positive electrode, the opening of the ground plate electrode and the spark zone are located within the second portion of the conduit capable of emitting a plasma.

A capacitative circuit electrically coupled to a high voltage power supply to provide a voltage of at least 500 V can be repeatedly charging and discharging across the positive and ground negative to give rise to a pulsed spark discharge at a rate of at least 1 Hz in the spark zone. A gas flows through the spark zone simultaneously with the creation of the pulsed spark discharge to give rise to a non-thermal plasma emitted from the second portion of the conduit, the non-thermal plasma comprising NO. Finally, a skin ulcer is contacted with the non-thermal plasma for sufficient time and intensity to give rise to treatment of the skin ulcer.

In some embodiments it is desirable that the cold spark discharge voltage is in the range of from about 500 V to about 5 kV. The diameter of the non-thermal plasma is suitably in the range of from about 3 mm to about 5 mm. A suitable pulsed spark discharge is pulsed at a frequency in the range of from about 1 Hz to about 7 Hz. The duration of the pulsed spark discharge can be in the range of from about 5 microseconds to 50 microseconds. Each pulsed spark discharge is characterized as having an energy per pulse in the range of from about 0.1 J to about 2 J.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed:

1. A method of treating a biological tissue using non-thermal plasma, comprising:
    flowing a gas through a cold spark discharge zone simultaneously with the creation of a pulsed spark discharge to give rise to a non-thermal plasma emitted from a conduit, the nonthermal plasma comprising a predetermined concentration of nitric oxide (NO); and
    contacting a wound on the biological tissue with said non-thermal plasma for sufficient time and intensity to give rise to healing of the wound;
    wherein the cold spark discharge voltage is in the range of 500 V to 5 kV;
    wherein the diameter of the non-thermal plasma is in the range of 3 mm to 5 mm;
    wherein the duration of the pulsed spark discharge is in the range of from 5 microseconds to 50 microseconds and is pulsed at a frequency in the range of 1 Hz to 30 Hz.

2. The method of claim 1, wherein the pulsed spark discharge is pulsed at a frequency in the range of from 1 Hz to 7 Hz.

3. The method of claim 1, wherein each pulsed spark discharge is characterized as having an energy per pulse in the range of from 0.1 J to 2 J.

4. The method of claim 1, where the biological tissue is skin, and the step of contacting the wound includes a step of contacting a skin ulcer with the non-thermal plasma for sufficient time and intensity to give rise to healing of the skin.

5. The method of claim 1, wherein the predetermined concentration of NO is 300 ppm.

6. The method of claim 1, wherein the predetermined concentration of NO is 500 ppm.

7. A method of treating a skin ulcer using non-thermal plasma, comprising:

flowing a gas through a conduit capable of fluidically communicating gas, plasma, or both gas and plasma, therethrough, a first portion of the conduit capable of being connected to a gas supply, and a second portion of the conduit capable of emitting a plasma, the conduit comprising therewithin:

a positive electrode comprising a sharp tip, the positive electrode capable of receiving a high voltage from a positive terminal of a high voltage power supply;

a ground plate electrode comprising an opening passing through the plate, the opening characterized as having a dimension, d, the ground plate electrode capable of being in electrical communication with ground and a negative electrode of said high voltage power supply, the sharp tip of the positive electrode being axially displaced from the opening of the ground plate electrode by distance h, the distance h defining a spark zone between the sharp tip of the positive electrode and the opening of the ground plate electrode;

wherein the sharp tip of the positive electrode, the opening of the ground plate electrode and the spark zone are located within the second portion of the conduit capable of emitting a plasma; and repeatedly charging and discharging a capacitative circuit electrically coupled to a high voltage power supply to provide a voltage of at least 500 V across the positive and ground negative to give rise to a pulsed spark discharge at a rate of at least 1 Hz in the spark zone;

flowing the gas through the spark zone simultaneously with the creation of the pulsed spark discharge to give rise to a non-thermal plasma emitted from the second portion of the conduit, the non-thermal plasma comprising a predetermined concentration of nitric oxide (NO); and contacting a skin ulcer with said non-thermal plasma for sufficient time and intensity to give rise to healing of the skin ulcer, wherein the cold spark discharge voltage is in the range of from about 500 V to about 5 kV, wherein the diameter of the non-thermal plasma is in the range of from about 3 mm to about 5 mm, wherein the pulsed spark discharge is pulsed at a frequency in the range of from about 1 Hz to about 30 Hz, and wherein the duration of the pulsed spark discharge is in the range of from about 5 microseconds to about 50 microseconds.

8. The method of claim 7, wherein the distance h is in a range of from 1 mm to 3 mm.

9. The method of claim 7, wherein the pulsed spark discharge is pulsed at a frequency in the range of from 1 Hz to 7 Hz.

10. The method of claim 7, wherein each pulsed spark discharge is characterized as having an energy per pulse in the range of from 0.1 J to 2 J.

11. The method of claim 7, wherein the positive electrode comprising the sharp tip is in a coaxial configuration with the conduit.

12. The method of any one of claim 4 or 7, wherein the skin ulcer is caused by diabetes, cancer, a burn, pressure, or any combination thereof.

13. The method of claim 7, wherein the predetermined concentration of NO is 300 ppm.

14. The method of claim 7, wherein the predetermined concentration of NO is 500 ppm.

* * * * *